(12) United States Patent
Shida et al.

(10) Patent No.: US 7,972,872 B2
(45) Date of Patent: Jul. 5, 2011

(54) CHROMATOGRAPHY DETECTION APPARATUS, DETECTION METHOD, AND KIT UTILIZING THE SAME

(75) Inventors: Ryo Shida, Niigata (JP); Hiromi Ito, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 473 days.

(21) Appl. No.: 11/628,621

(22) PCT Filed: Jun. 7, 2005

(86) PCT No.: PCT/JP2005/010386
§ 371 (c)(1),
(2), (4) Date: Dec. 6, 2006

(87) PCT Pub. No.: WO2005/121794
PCT Pub. Date: Dec. 22, 2005

(65) Prior Publication Data
US 2008/0194013 A1    Aug. 14, 2008

(30) Foreign Application Priority Data
Jun. 7, 2004 (JP) .................. 2004-169200

(51) Int. Cl.
*G01N 33/53* (2006.01)
(52) U.S. Cl. ........ 436/518; 436/514; 436/164; 436/169; 436/524; 436/529; 436/530; 436/805; 436/810; 435/287.1; 435/287.2; 435/287.7; 435/287.9; 435/970; 435/805; 435/810; 422/420; 422/422; 422/425; 422/427; 422/430
(58) Field of Classification Search ............... 435/287.1, 435/287.2, 287.7, 287.9, 970, 805, 810; 436/514, 436/518, 164, 169, 524, 529, 530, 805, 810; 422/56–61
See application file for complete search history.

(56) References Cited

U.S. PATENT DOCUMENTS
4,105,499 A * 8/1978 Kiyasu .......................... 435/17
(Continued)

FOREIGN PATENT DOCUMENTS
DE    42 38 806 A1    5/1993
(Continued)

OTHER PUBLICATIONS
European Search Report Application No. 09003334.1 Dated May 19, 2009.
(Continued)

*Primary Examiner* — Bao-Thuy L Nguyen
(74) *Attorney, Agent, or Firm* — Stephen A. Bent; Foley & Lardner LLP

(57) ABSTRACT

This invention provides an immunochromatography detection apparatus exhibiting excellent convenience, sensitivity, and specificity, a detection method therefore, a kit using the same, and a method for producing such apparatus and kit, by constructing a solid-phase support, on which the conditions for the reaction wherein an analyte specifically binds to a labeled reagent containing a ligand that specifically binds to the analyte and those for the reaction wherein a capture reagent specifically binds to a complex of the analyte and the labeled reagent in the immunochromatography detection method are continuously optimized, and the pretreated specimens are optimized for such reactions. This chromatography detection apparatus comprises: a sheet-like solid-phase support; a specimen-supply site thereon at which a specimen deduced to contain at least an analyte or a mixture of such specimen and a labeled reagent containing a ligand that specifically binds to the analyte is supplied; and a capture reagent site to which a capture reagent capable of specifically binding to and capturing a complex of the analyte and the labeled reagent has been immobilized, wherein at least one functional site having a particular or multiple functions is provided between the specimen-supply site and the capture reagent site.

7 Claims, 8 Drawing Sheets

U.S. PATENT DOCUMENTS

| | | | |
|---|---|---|---|
| 4,652,517 A * | 3/1987 | Scholl et al. | 435/5 |
| 5,858,645 A * | 1/1999 | Kuzuya et al. | 435/4 |
| 6,008,059 A | 12/1999 | Schrier et al. | |
| 6,017,767 A | 1/2000 | Chandler | |
| 6,197,598 B1 | 3/2001 | Schrier et al. | |
| 6,703,196 B1 | 3/2004 | Klepp et al. | |
| 6,737,277 B1 * | 5/2004 | Kang et al. | 436/514 |
| 7,378,285 B2 * | 5/2008 | Lambotte et al. | 436/514 |
| 2004/0038295 A1 | 2/2004 | Rademacher et al. | |

FOREIGN PATENT DOCUMENTS

| | | |
|---|---|---|
| JP | 11-505327 | 5/1999 |
| JP | 11-248708 | 9/1999 |
| JP | 2002-202308 | 7/2002 |
| JP | 2003-532896 | 11/2003 |
| WO | WO 88/02028 | 3/1988 |

OTHER PUBLICATIONS

Matthias Cavassini et al., "Evaluation of MRSA-Screen, a Simple Anti-PBP 2a Slide Latex Agglutination Kit, for Rapid Detection of Methicillin Resistance in *Staphylococcus aureus*", Journal of Clinical Microbiology, May 1999, vol. 37, No. 5, pp. 1591-1594.

* cited by examiner

Fig. 1
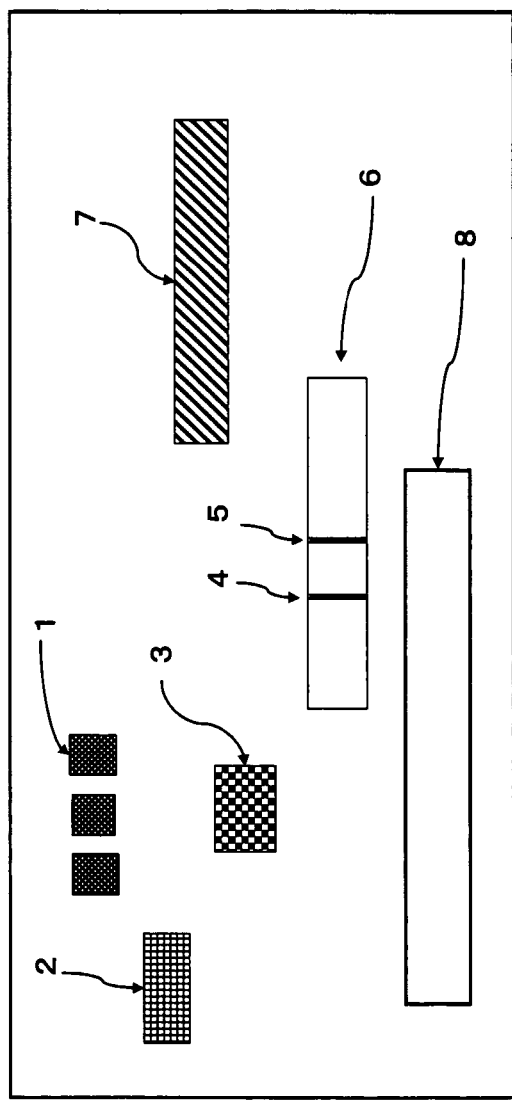
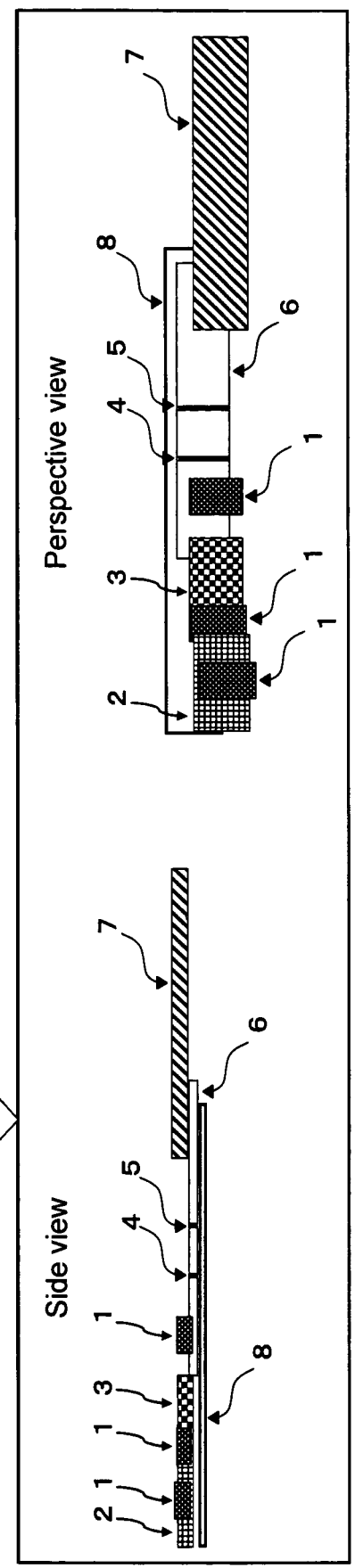

CHROMATOGRAPHY DETECTION APPARATUS, DETECTION METHOD, AND KIT UTILIZING THE SAME

TECHNICAL FIELD

The present invention relates to a chromatography detection apparatus for conducting qualitative or quantitative assay that specifically detects an analyte in a sample, a detection method therefor, and a kit using the same.

BACKGROUND ART

As methods of analysis for detecting or quantifying an analyte in a sample with the utilization of immune response specificity, a variety of methodologies, such as immunodiffusion, enzyme assay, and aggregation, have been put to practical use. In particular, detection methods by means of immunochromatography assay (detection) techniques (a lateral-flow assay, a tangential-flow assay, JP Patent Publication (Kokoku) No. 7-13640B (1995), JP Patent No. 2,131,938, and JP Patent No. 2,890,384) spread rapidly because of the convenience thereof in recent years.

The principles of such detection methods are briefly described below. Many types of commercial kits for immunochromatography assay techniques each comprise a sheet-like solid-phase support. On the sheet-like solid-phase support, the following members are sequentially immobilized from an end thereof in the lengthwise direction: 1. a specimen-supply site; 2. a labeled reagent site that holds on a membrane a labeled reagent (e.g., colloidal gold particles that can be visualized or enzymes) containing a ligand that specifically binds to an analyte (e.g., an antigen) so as to be capable of developing on the membrane; and 3. a capture reagent site to which a capture reagent (e.g., an antibody) has been immobilized for capturing an analyte (e.g., an antigen) or label antibody or a complex of the analyte and the label reagent. In such a kit, a solution is continuously transferred via capillary action.

If a given amount of a sample comprising an analyte-containing specimen suspended therein is supplied to the site to which the analyte has been applied, the sample migrates into the site to which the labeled reagent has been applied while developing on the solid-phase support, and the analyte binds to a labeled reagent to form a complex of the analyte and the label reagent. The complex of the analyte and the label reagent develops on the membrane and migrates into the capture reagent site on the membrane, the complex is captured by the capture reagent immobilized on the solid-phase support, and the complex of the capture reagent, the analyte, and the labeled reagent is formed at the capture reagent site. The presence of the analyte can be determined by detecting the labeled reagent by any technique (in the case of colloidal gold particles that can be visualized, an image of the aggregate thereof is to be detected; in the case of enzymes, color development resulting from the addition of a support is to be detected). FIG. 7 shows a conventional immunochromatography detection apparatus.

Because of its constitution, an immunochromatography detection apparatus involves the supply and the development of a specimen on a solid-phase support. This enables the continuous and automatic performance of the following reactions on the solid-phase support: (A) the reaction wherein an analyte specifically binds to a labeled reagent containing a ligand that specifically binds to the analyte; and (B) the reaction wherein a capture reagent specifically binds to the complex of the analyte and the labeled reagent. Thus, detection methods involving the use of such immunochromatography apparatus are excellent in terms of convenience. In fact, however, many detection processes suffer from the presence of impurities in the analyte-containing specimens. Thus, pretreatments such as separation and extraction of analytes from specimens were required in order to remove such impurities via a variety of chemical or physical treatment prior to the assay. In such a case, pretreatments were often conducted under conditions that were not optimal for the binding between the antigen and the antibody. Accordingly, the specimens were required to be optimized for the binding, following the pretreatments. In order to facilitate specific binding of the analyte to the labeled reagent, a pH level, a salt concentration, and other conditions had to be controlled in the reaction system. Since the optimal reaction conditions such as a pH level or a salt concentration of the reaction (A) were not always consistent with those of the reaction (B), such technique was disadvantageous compared with other detection techniques involving a plurality of separate reactions, such as ELISA, in terms of convenience, sensitivity, and specificity.

Patent Document 1: JP Patent Publication (Kokoku) No. 7-13640B (1995)
Patent Document 2: JP Patent No. 2,131,938
Patent Document 3: JP Patent No. 2,504,923
Patent Document 4: JP Patent No. 2,890,384

DISCLOSURE OF THE INVENTION

The present invention provides an immunochromatography detection apparatus exhibiting excellent convenience, sensitivity, and specificity, a detection method therefor, a kit using the same, and a method for producing such apparatus and kit, by constructing a solid-phase support, on which the conditions for the reaction wherein an analyte specifically binds to a labeled reagent containing a ligand that specifically binds to the analyte and those for the reaction wherein a capture reagent specifically binds to a complex of the analyte and the labeled reagent in the immunochromatography detection method are continuously optimized, and the pretreated specimens are optimized for such reactions. Further, the present invention provides an immunochromatography detection apparatus capable of pretreating the specimens on the solid-phase support, the detection method therefor, the kit using the same, and the method for producing such apparatus and kit.

The present inventors have conducted concentrated studies in order to develop an immunochromatography detection apparatus exhibiting excellent promptness, convenience, sensitivity and specificity by constructing a solid-phase support, on which the conditions for the reaction wherein an analyte specifically binds to a labeled reagent containing a ligand that specifically binds to the analyte and those for the reaction wherein a capture reagent specifically binds to the complex of the analyte and the labeled reagent in the immunochromatography detection method are continuously optimized, and the pretreated specimens are optimized for such reactions. As a result, they discovered that an immunochromatography detection method exhibiting excellent convenience, sensitivity, and specificity could be carried out by incorporating a means of optimizing each reaction condition into a solid-phase support when the aforementioned reactions continuously take place after the application of the specimens to the application site. The present inventors completed the present invention by providing a member having a function of optimizing the reaction conditions and/or a reagent-containing functional site on the solid-phase support as a means of optimizing the reaction conditions. Further, the present inventors discovered that detection could be carried out without the necessity of pretreating the specimens prior to the addition thereof to the application site by providing a member having a means of treating specimens and/or a reagent-containing functional site on the solid-phase support. This has led to the completion of the present invention.

Specifically, the present invention is as follows.

[1] A chromatography detection apparatus comprising: a sheet-like solid-phase support; a specimen-supply site thereon at which a specimen suspected of containing at least an analyte or a mixture of such specimen and a labeled reagent containing a ligand that specifically binds to the analyte is supplied; and a capture reagent site to which a capture reagent capable of specifically binding to and capturing a complex of the analyte and the labeled reagent has been immobilized, wherein at least one functional site having at least one of the following functions (a) to (c) is provided between the specimen-supply site and the capture reagent site:

(a) a function of pretreating a specimen;

(b) a function of optimizing the reaction conditions wherein the analyte contained in the specimen specifically binds to a labeled reagent containing a ligand that specifically binds to the analyte; and (c) a function of optimizing the reaction conditions wherein a capture reagent specifically binds to the complex of the analyte and the labeled reagent.

[2] The chromatography detection apparatus according to [1], which comprises: a sheet-like solid-phase support; a specimen-supply site thereon at which a specimen suspected of containing at least an analyte is supplied; a labeled reagent site at which a labeled reagent containing a ligand that specifically binds to the analyte is held so as to be capable of developing on the solid-phase support; and a capture reagent site at which a capture reagent capable of specifically binding to and capturing the complex of the analyte and the labeled reagent has been immobilized.

[3] The chromatography detection apparatus according to [1], wherein the analyte is brought into contact with the labeled reagent in advance at a site detached from the solid-phase support, and a mixture of a specimen suspected of containing an analyte and a labeled reagent containing a ligand that specifically binds to the analyte is supplied to the specimen-supply site.

[4] The chromatography detection apparatus according to [1] or [2], wherein the specimen-supply site is provided at a site spatially separate from the labeled reagent site.

[5] The chromatography detection apparatus according to any of [1] to [4], wherein the function of pretreating a specimen is for removing impurities from the specimen and/or for extracting an analyte from the specimen.

[6] The chromatography detection apparatus according to [5], wherein the function of pretreating a specimen is for extracting an analyte, and a functional site for pretreating a specimen comprises a reagent for extracting an analyte from the specimen.

[7] The chromatography detection apparatus according to [6], wherein the reagent for extracting an analyte from a specimen is a basic substance, acidic substance, or surfactant for extracting an analyte from a biological matrix in a biological matrix-containing specimen via alkaline, acid, or surfactant treatment.

[8] The chromatography detection apparatus according to any of [5] to [7], wherein the function of pretreating a specimen is for removing impurities from the specimen, and the functional site for pretreating a specimen is capable of filtering, adsorbing, or aggregating impurities contained in the specimen.

[9] The chromatography detection apparatus according to [8], wherein the functional site having a function of pretreating a specimen is a filter, and this filter removes impurities from the specimen.

[10] The chromatography detection apparatus according to [8] or [9], wherein the functional site having a function of pretreating a specimen comprises a reagent for adsorbing or aggregating impurities.

[11] The chromatography detection apparatus according to [10], wherein the functional site having a function of pretreating a specimen comprises a reagent for adsorbing or aggregating impurities, and the reagent for adsorbing or aggregating impurities is contained in the solid-phase support.

[12] The chromatography detection apparatus according to [11], wherein the reagent for adsorbing or aggregating impurities is contained between the specimen-supply site and the labeled reagent site on the solid-phase support.

[13] The chromatography detection apparatus according to any of [1] to [12], wherein the functional site having a function of optimizing the reaction conditions comprises a reagent for optimizing the reaction conditions.

[14] The chromatography detection apparatus according to [13], wherein the reagent for optimizing the reaction conditions adjusts the pH level in the reaction system to a range optimal for the reaction.

[15] The chromatography detection apparatus according to [13], wherein the reagent for optimizing the reaction conditions adjusts the salt concentration in the reaction system to a range optimal for the reaction.

[16] The chromatography detection apparatus according to any of [13] to [15], wherein the reagent is selected from the group consisting of a buffer, an acidic reagent, a basic reagent, and a surfactant.

[17] The chromatography detection apparatus according to any of [13] to [16], which comprises a functional site for optimizing the conditions of the reaction wherein the analyte contained in the pretreated specimen binds to a ligand or capture reagent.

[18] The chromatography detection apparatus according to any of [13] to [17] comprising a plurality of capture reagent sites capable of capturing different analytes, wherein at least one capture reagent site comprises upstream thereof a reagent for optimizing the conditions of the reaction wherein the capture reagent binds to the analyte.

[19] The chromatography detection apparatus according to [18], wherein each analyte is capable of cross-reacting with a corresponding capture reagent, and the cross reaction is inhibited by optimizing the conditions of the binding reaction.

[20] The chromatography detection apparatus according to any of [5] to [19], wherein the specimen contains bacteria or viruses, and the functional site having a function of pretreating a specimen has a function of extracting an analyte from the bacteria or viruses.

[21] The chromatography detection apparatus according to [20], which further comprises a functional site for optimizing the conditions of the reaction wherein the analyte in the pretreated specimen binds to a ligand or capture reagent.

[22] The chromatography detection apparatus according to any of [5] to [21], wherein the specimen is a nasal or throat swab, the functional site having a function of pretreating a specimen comprises a reagent for aggregating a polysaccharide in a nasal or throat swab, and the apparatus comprises a filter for removing aggregated polysaccharides.

[23] The immunochromatography detection apparatus according to any of [5] to [21], wherein the analyte contains influenza A virus antigen and influenza B virus antigen, the apparatus comprises a capture reagent site for capturing influenza A virus antigen and a capture reagent site for capturing influenza B virus antigen, which comprises functional sites containing reagents capable of inhibiting binding via cross reaction to capture reagents capable of capturing influenza A virus antigens and influenza B virus antigens and/or binding via cross reaction of influenza B virus antigen with capturing reagents capable of capturing influenza A virus antigen.

[24] The chromatography detection apparatus according to any of [1] to [23], wherein the labeled reagent is a ligand labeled with an enzyme or insoluble particulate substance.

[25] The chromatography detection apparatus according to any of [1] to [24], wherein the binding between the analyte and the ligand and the binding between the analyte-ligand complex and the capture reagent result from the antigen-antibody reaction.

[26] The chromatography detection apparatus according to any of [1] to [25], wherein the solid-phase support is selected from the group consisting of nitrocellulose, cellulose acetate, nylon, and polyethersulfone.

EFFECTS OF THE INVENTION

The use of the immunochromatography apparatus of the present invention can continuously optimize the conditions for the reaction wherein an analyte specifically binds to a labeled reagent containing a ligand that specifically binds to the analyte and those for the reaction wherein a capture reagent specifically binds to the complex of the analyte and the labeled reagent on the solid-phase support of the immunochromatography detection apparatus. This enables the performance of detection with excellent promptness, convenience, sensitivity, and specificity. Also, a specimen that became unsuitable for the reaction due to the pretreatment can be optimized on the solid-phase support. This enables prompt detection. Further, the apparatus of the present invention comprises a means of treating a specimen and a means of optimizing the treated specimen for the reactions. This enables the performance of the detection with more promptness and higher sensitivity.

This description includes part or all of the contents as disclosed in the description and/or drawings of Japanese Patent Application No. 2004-169200, which is a priority document of the present application.

BRIEF DESCRIPTION OF THE DRAWINGS

FIG. 1 shows an embodiment of the detection apparatus of the present invention.

DESCRIPTION OF REFERENCE NUMERALS

Figure 2:
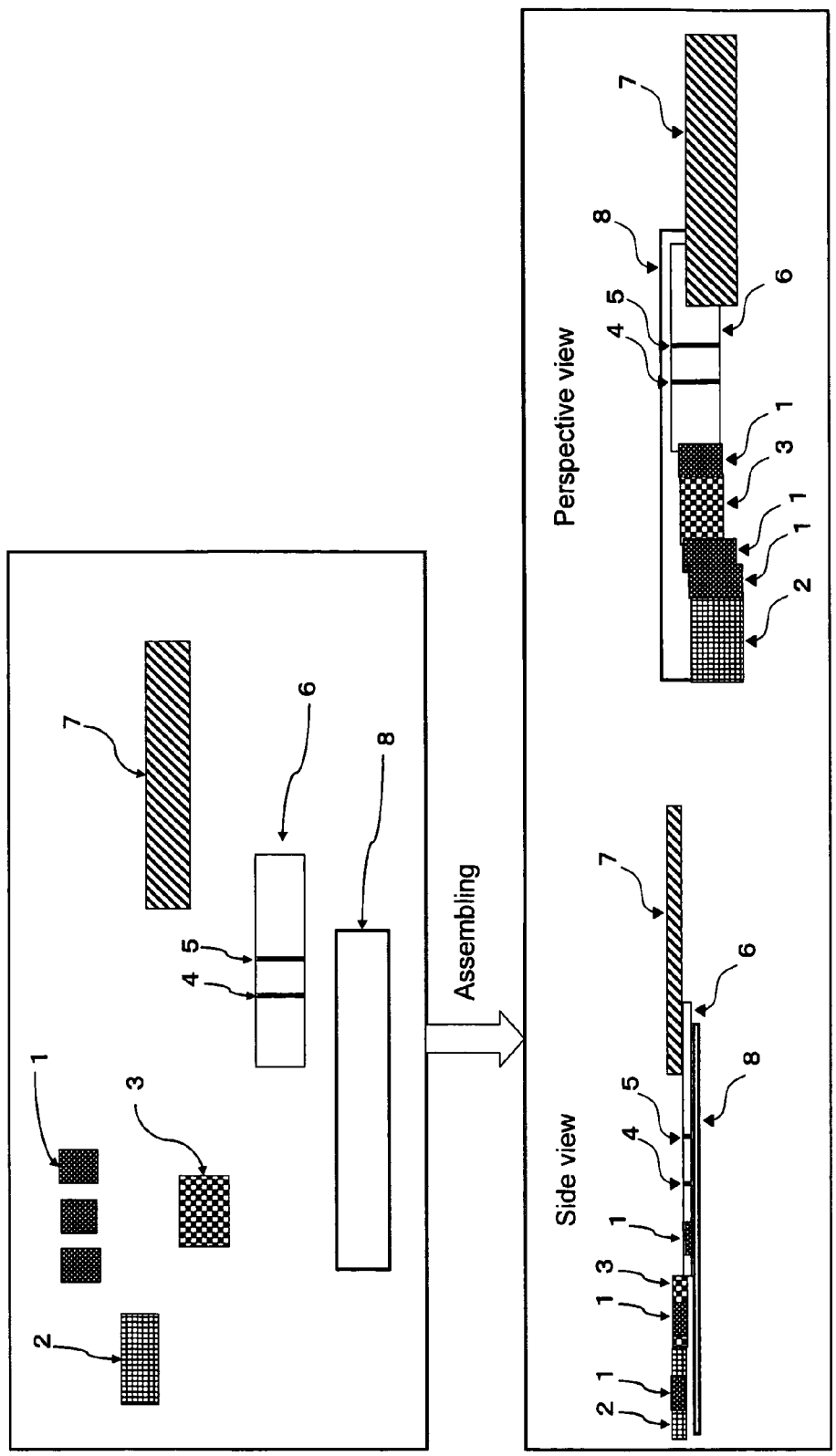
FIG. 2 shows an embodiment of the detection apparatus of the present invention.

1: Functional site
2: Specimen-supply site
3: Labeled reagent site
4: Capture reagent (capture antibody) site
5: Control site
6: Solid-phase support (nitrocellulose membrane)
7: Absorption site (absorbent pad)
8: Top laminate or housing

PREFERRED EMBODIMENT OF THE INVENTION

Hereafter, the present invention is described in detail.

The present invention provides an apparatus that detects an analyte in a specimen. More particularly, the present invention provides an immunochromatography detection apparatus, a detection method, and a kit using the same. The detection apparatus of the present invention comprises: a sheet-like solid-phase support; a specimen-supply site thereon at which a specimen suspected of containing at least an analyte or a mixture of such specimen and a labeled reagent containing a ligand that specifically binds to the analyte is supplied; and a capture reagent site to which a capture reagent capable of specifically binding to and capturing a complex of the analyte and the labeled reagent has been immobilized. When a specimen suspected of containing an analyte is supplied to the specimen-supply site, the specimen passes through the labeled reagent site and the capture reagent site in that order. The apparatus of the present invention may further comprise a labeled reagent site that holds a labeled reagent containing a ligand that specifically binds to the analyte so as to be capable of developing on a solid-phase support. In such a case, the specimen binds to the labeled reagent on the solid-phase support. Thus, a specimen may be selectively supplied to the specimen-supply site.

The apparatus of the present invention comprises a means of optimizing the binding reactions that take place on the solid-phase support, such as antigen-antibody reactions. Specifically, while the specimen is supplied to the specimen-supply site, it develops on the solid-phase support to the labeled reagent site, and the analytes in the specimens specifically bind to the labeled reagent to form a complex of the analyte and the labeled reagent, the analyte is separated from the specimen, and the conditions are modified so as to facilitate the specific binding of the labeled reagent to the analyte with the aid of at least one member- or reagent-containing functional site provided in advance between the specimen-supply site and the labeled reagent site on the solid-phase support. While a capture reagent specifically binds to the complex to form a complex of the analyte, the labeled reagent, and the capture reagent, the complex is brought into contact with at least one member- or reagent-containing functional site provided in advance between the labeled reagent site and the capture reagent site on the solid-phase support. This facilitates the specific binding of the capture reagent to the complex while the complex develops on the solid-phase support to the capture reagent site. Further, the apparatus of the present invention comprises a means of optimizing the conditions (e.g., pH levels) of the specimen that became unsuitable for the binding reactions, such as antigen-antibody reactions, due to pretreatment such as acid or alkaline treatment. More specifically, while the specimen is supplied to the specimen-supply site, it develops on the solid-phase support to the labeled reagent site, the analyte in the specimen specifically binds to the labeled reagent to form a complex of the analyte and the labeled reagent, and the conditions are optimized with the aid of at least one member- or reagent-containing functional site provided in advance between the specimen-supply site and the labeled reagent site on the solid-phase support. Furthermore, the apparatus of the present invention comprises a means of pretreating a specimen. The term "pretreating" or "pretreatment" refers to extraction or isolation of an analyte from a specimen and removal of impurities from the specimen.

The means of optimizing the binding reactions that take place on the solid-phase support, such as antigen-antibody reactions, the means of optimizing the conditions of the specimen, and the means of pretreating the specimen of the apparatus of the present invention each comprise a functional site containing a member or reagent having a relevant function.

In the apparatus of the present invention, the specimen-supply site may be an end of the solid-phase support. Alternatively, such site may be composed of a member composed of a member different from that of the solid-phase support, natural or synthetic polymers such as nitrocellulose, cellulose acetate, nylon, polyethersulfone, polyvinyl alcohol, polyester, glass fiber, polyolefin, cellulose, or polystyrene or a mixture of any of such substances. Such site is provided on the solid-phase support in a manner such that it absorbs a specimen or a mixture of the specimen and the labeled reagent and the absorbed specimen or mixture is supplied to the solid-phase support, and a solution is capable of developing on the solid-phase support due to the capillary flow. The specimen-supply site may comprise a reagent that regulates or optimize the aforementioned reaction conditions; i.e., the specimen-supply site may also serve as a functional site. When the specimen-supply site is directly soaked in a developer, the reagent incorporated into the specimen-supply site is discharged in the developer. Thus, it is preferable that the specimen-supply site be independently provided. The labeled reagent site may be prepared by coating the solid-phase support with the labeled reagent and then drying the support. Also, the labeled reagent may be incorporated into the aforementioned member, which is different from the solid-phase support, and then dried, and the resultant may be provided on the solid-phase support or connected in series with the solid-phase support. Similarly, the capture reagent site may be provided by coating the solid-phase support with the capture reagent and then drying the support. Also, the capture reagent may be incorporated into the aforementioned member, which is different from the solid-phase support, and then dried, and the resultant may be provided on the solid-phase support or connected in series with the solid-phase support (FIGS. 1 and 2).

According to the method of the present invention, a specimen that is suspected of containing an analyte is first supplied to the specimen-supply site. An analyte to be analyzed by the method of the present invention is not limited. In general, such an analyte is an antigen or antibody. A specimen is not limited, and examples thereof include: biological samples, such as whole blood, blood serum, blood plasma, urine, saliva, sputum, nasal or throat swab, sweat, or stool; food extracts, such as meat or vegetable extracts; environmental samples obtained from a drainage, mud, or soil; culture solutions or suspensions of microorganisms, such as bacteria or viruses; and extract of bacteria or viruses.

A specimen may be directly supplied to the specimen-supply site without any treatment such as dilution. Concerning the specimens that cannot easily develop on a solid-phase support due to viscosity or other conditions, the specimen may be diluted with a developer in advance. Alternatively, a sampling tool such as a cotton swab used to sample the specimen may be brought into direct contact with the specimen-supply site and the developer is supplied to the sampling tool, and the specimen adhered to the cotton swab is washed to supply the washing liquid to the specimen-supply site. The developer may have any composition as long as the analyte can develop on the solid-phase support without difficulty during the step of detection. Examples of such a developer include a variety of buffer solutions such as an acidic agent, a basic agent, a surfactant, and a denaturing agent.

The analyte in the specimen that had been supplied to the specimen-supply site in accordance with the aforementioned method develops on the solid-phase support to form a complex of the analyte and the labeled reagent at a site that holds a labeled reagent (i.e., the labeled reagent site). The resulting complex is captured by a capture reagent at a capture reagent site and then immobilized on the solid-phase support.

In this case, the specimen-supply site and the labeled reagent site may be the same site or different sites spatially separate from each other. When these sites are different from each other, these sites may be in partial contact with each other via capillary flow. Alternatively, these sites may be intervened with the solid-phase support or functional site and thus they are not in contact with each other, through which these sites may be communicated with each other via capillary flow. The phrase "communicated . . . via capillary flow" used herein refers to the phenomenon that a fluid such as a specimen is capable of developing between the communicated sites due to the capillary phenomenon. In the apparatus of the present invention, the analyte may be brought into contact with the labeled reagent in advance at a site separate from the solid-phase support. This indicates that the labeled reagent is not incorporated in the solid-phase support or that the labeled reagent is not incorporated in the site that is in contact with the solid-phase support and the liquid is communicable with the solid-phase support, such as the specimen-supply site. In such a case, the analyte is brought into contact with the labeled reagent in advance at a site other than the solid-phase support and a site other than that in contact with the solid-phase support. In the case of some conventional immunochromatography detection apparatuses, for example, a solid-phase support is in contact with a porous support containing a labeled reagent. In such conventional apparatuses, a porous support containing a labeled reagent serves also as a specimen-supply site. Upon the addition of the specimen to the specimen-supply site, the specimen is brought into contact with the labeled reagent, and the mixture of the specimen and the labeled reagent immediately develops to the solid-phase support. That is, the specimen is brought into contact with the labeled reagent at a site that is in contact with the solid-phase support. In the present invention, however, a mixture of the specimen is brought into contact with the labeled reagent at a site separate from the solid-phase support, i.e., other than the solid-phase support and a site in contact with the solid-phase support, in order to regulate the contact time between the specimen and the labeled reagent, unlike conventional apparatus. The labeled reagent may be brought into contact with the specimen in a device for supplying a specimen, for example. The device for supplying a specimen is a component provided outside the detection apparatus, and such a device is a container for accommodating the recovered specimen and performing specific processing thereon. The device comprises a vial, a syringe, a tube, or the like. In addition to a container, the device may comprise a means of filtration for filtering a specimen at the time of supply of the specimen to the detection apparatus. The device for supplying a specimen comprises a container for accommodating a specimen and a section for supplying the specimen contained in the container to the detection apparatus. The section for supplying the specimen comprises a section having a nozzle (a spout) for discharging the specimen from the container, and such a section can also serve as a cover for the container. The section for supplying the specimen is also referred to as a nozzle section or a cover section. When the device for supplying a specimen comprises a means of filtration, the device may be composed of two sections, i.e., a nozzle section composed of a filter housing comprising a filter and a container. In such a case, the filter housing comprises an opening for allowing the specimen to pass through the filter and an opening for discharging the filtered specimen, and a filter is provided between these openings. The container may be a syringe that allows the specimen to pass through the filter with pressurization, for example.

In the apparatus of the present invention, the analyte is brought into contact, in advance, with at least one functional site containing a member, reagent, or both thereof for regulating and optimizing the conditions provided at any position on the solid-phase support or the analyte passes through the functional site while the analyte develops on the solid-phase support to form a complex of the analyte and the labeled reagent at a labeled reagent site, the resulting complex is captured by a capture reagent at a capture reagent site and then immobilized on the solid-phase support. The functional site containing the aforementioned member or reagent may be provided between the specimen-supply site and the labeled reagent site or between the labeled reagent site and the capture reagent site, according to need. In the case of "between the specimen-supply site and the labeled reagent site," the apparatus comprises the specimen-supply site or labeled reagent site. In such a case, the specimen-supply site or labeled reagent site serves also as a functional site containing the aforementioned member or reagent. Specifically, the specimen-supply site or labeled reagent site may be constructed using a member having a specific function, or the specimen-supply site or labeled reagent site may be impregnated with a reagent having a specific function.

Examples of a member constituting a functional site to be provided on the solid-phase support in advance include, but are not limited to, nitrocellulose, cellulose acetate, nylon, polyethersulfone, polyvinyl alcohol, polyester, glass fiber, polyolefin, cellulose, and artificial polymers composed of mixtures of the above fibers. When a functional site is provided with a function of filtration, for example, any member that can act as a filter can be used. Such member can contain a reagent that not only filters a liquid developing on the solid-phase support but also regulates the reaction conditions. Such functional site is communicated with the solid-phase support via capillary flow and is positioned in a manner such that the solution can pass through the functional site and develop on the solid-phase support. Examples of a reagent contained in the functional site include chemicals, such as an acidic agent, a basic agent, a surfactant, and a denaturing agent, and biochemical reagents, such as an enzyme, an antibody, biotin, avidin, and protein A. If a reagent is positioned so as to be brought into contact with the specimen while the specimen develops on the solid-phase support, the solid-phase support may be coated with the reagent and then dried. Alternatively, the member may be impregnated with the reagent and dried, and the resultant may then be provided on the solid-phase support, or such member may be connected in series with the solid-phase support in such a manner that the member is communicated with the solid-phase support via capillary flow. FIGS. 1 and 2 each show an embodiment of the apparatus of the present invention. As shown in the figures, a plurality of functional sites can be provided. The positions of the functional sites can be adequately determined. As the right functional site shown in FIG. 1, a functional site may be mounted on the solid-phase support. Also, a functional site may be provided in the solid-phase support in such a manner that the member is communicated with the solid-phase support via capillary flow, as the right functional site shown in FIG. 2. In such a case, a material constituting a member of a functional site may be the same with or different from a material constituting the solid-phase support. In the case of the right functional site shown in FIG. 2, all the fluids such as developing specimens are brought into contact with and pass through the functional site. This can yield more significant effects. Without the use of a member constituting a functional site, a functional site may be directly incorporated in the solid-phase support. For example, a substance that is capable of adsorbing and removing impurities described below may be incorporated by coating or impregnating the solid-phase support with such substance. A functional site may be incorporated in a site between the specimen-supply site and a labeled reagent site or a site between a labeled reagent site and a capture reagent site on the solid-phase support. The site between the specimen-supply site and the labeled reagent site is preferable.

One of the functions of the functional site is that of pretreating a specimen. For example, such function is removal of impurities from a specimen by means of filtration or physical adsorption such as hydrophobic or electrostatic adsorption with the use of a material constituting a member of the functional site. The term "impurities" used herein refers to substances that are capable of inhibiting development of specimens on the solid-phase support or substances that are capable of inhibiting the reaction wherein an analyte specifically binds to a labeled reagent containing a ligand that specifically binds to the analyte on the solid-phase support and the reaction wherein a capture reagent specifically binds to the complex of the analyte and the labeled reagent. As described above, various substances may be employed as specimens and some specimens contain peculiar impurities. For example, a blood specimen contains fibrins and erythrocytes, a nasal or throat swab specimen contains a polysaccharide such as chondroitin sulfate, and a stool specimen contains various types of solid substances. With the use of porous fiber as a member of the functional site, such member can function as a filter and remove impurities from a specimen. By removing impurities, the analyte or the complex of the analyte and the labeled reagent is isolated and becomes capable of specifically binding to a labeled reagent or captured reagent. The other function of the functional site is to stably hold the reagent, when the functional site is impregnated with the reagent. The functional site also has a function of regulating the speed of development of a solution on the functional site and the solid-phase support and a function of regulating the duration of the action mechanism and the concentration gradient of a reagent contained in the functional site, depending on the amount of the solution absorbed.

A function of pretreating the functional site includes extraction of an analyte from a specimen. When an analyte in a clinical specimen is to be detected, such analyte is often present in a cell membrane, cell wall, cell organelle, or biological matrix, such as an intercellular substance, of a microorganism or cell. When bacterial or virus infection is to be detected, for example, a substance such as a protein existing in a cell wall of bacteria is detected in order to detect the presence of bacteria or viruses in the specimen. According to a conventional detection method, a specimen was pretreated in advance with an acid, an alkaline solution, or a surfactant, the substance existing in a cell membrane or cell wall was solubilized for extraction, and the extract was supplied to the specimen-supply site to detect a substance of interest. With the use of the apparatus of the present invention, an analyte can be extracted on the solid-phase support. Specifically, a specimen that develops on the solid-phase support is brought into contact with chemicals, such as an acidic agent, a basic agent, or a surfactant, and biochemical reagents, such as an enzyme, an antibody, biotin, avidin, or protein A contained in the functional site to destruct the microorganism or cell matrix, the destructed impurities are removed from the specimen via adsorption or other means, the analyte is selectively isolated, and the analyte then develops on the support.

Examples of the other function of the functional site include a function of adjusting the pH level and the inorganic salt concentration to an optimal range so as to facilitate specific binding reactions and a function of potentiating the specific reactions, when the analyte binds to the labeled reagent by the antigen-antibody reactions. The term "optimal range" used herein refers to a range with a given variability, within which the reaction is effectively carried out. Examples of reagents having such functions include a surfactant, a high-molecular-weight polymer, an acidic compound, and a basic compound. When the specimen is pretreated prior to the supply thereof to the detection apparatus or on the solid-phase support, for example, the antigen-antibody reaction is inhibited by an acid, alkali, or surfactant used in the pretreatment. In such a case, the acidified or basificated specimen can be neutralized by the apparatus of the present invention. Alternatively, a surfactant can be removed and the reaction can be performed under optimal conditions. The functional site also has a function of reducing nonspecific reaction. In this case, a reagent, such as a surfactant, high-molecular-weight polymer, or basic compound, is used. In the case of the multiassay intended to detect a plurality of analytes, the apparatus can be provided with a plurality of labeled reagent sites and a plurality of capture reagent sites on the solid-phase support. The apparatus can also be provided with functional sites each having a function of optimizing the reaction conditions at each capture reagent site or reducing the cross reaction of each reaction component. In such a case, a functional site is impregnated with a reagent, such as a surfactant, high-molecular-weight polymer, acidic compound, or basic compound, for adjusting the pH level and the inorganic salt concentration at each capture reagent site.

In the case of the apparatus shown in FIG. 1, for example, the leftmost functional site among the 3 functional sites is superposed on the specimen-supply site, and the middle functional site is partially in contact with and communicated with the specimen-supply site and the labeled reagent site via capillary flow. The right functional site is positioned at the labeled reagent site or at the captured reagent site on the solid-phase support. For example, the specimen is pretreated at the left functional site, the conditions such as a pH level of the pretreated specimen are adjusted at the middle functional site so as to optimize the binding reaction between the analyte and the labeled reagent, and the conditions are further adjusted at the right functional site so as to optimize the binding reaction between the analyte and the capture reagent. In the case of the apparatus shown in FIG. 1, the specimen-supply site is spatially separate from the labeled reagent site.

Hereafter, concrete embodiments of the present invention are described with reference to the figures.

Figure 3:
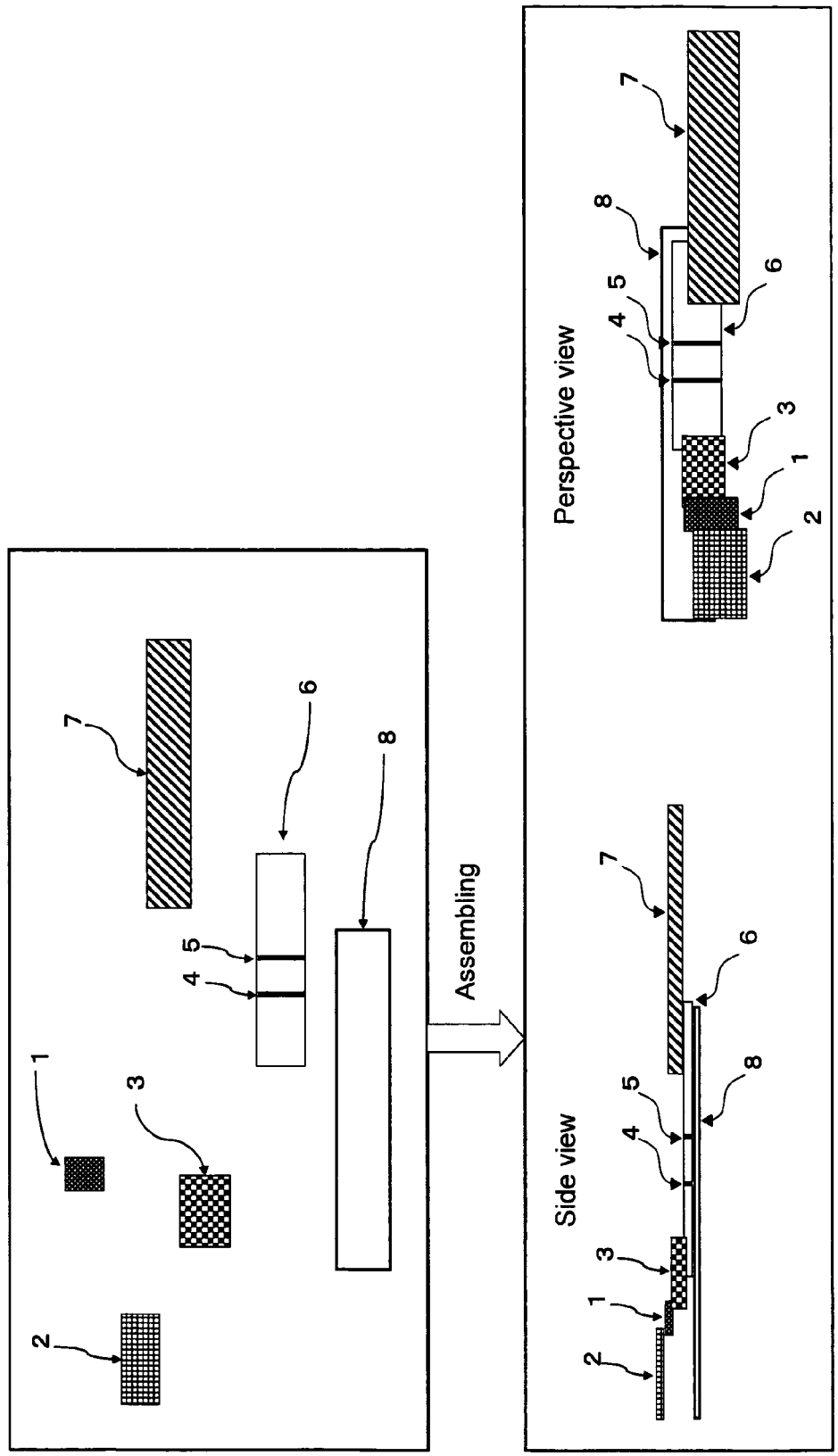
FIG. 3 shows a detection apparatus comprising a member having a function of filtering impurities.

FIG. 3 shows the apparatus of the present invention provided with a functional site having a function of filtering impurities. As an embodiment, detection of influenza viruses from a nasal or throat swab is shown. In this case, the functional site 1, which is porous and is provided with a function of filtration, is provided between the specimen-supply site 2 and the labeled reagent site 3. Such functional site 1 is prepared by impregnating porous fiber with a reagent, such as DEAE-Dextran, that aggregates a nonspecific reaction component contained in a nasal or throat swab, i.e., a mucopolysaccharide such as chondroitin sulfate, followed by drying. The throat swab specimen is suspended in any solution, and the resulting suspension is added to the specimen-supply site, or the specimen-supply site 2 is selectively immersed in the aforementioned suspension, to supply the specimen to the specimen-supply site 2. The specimen develops from the specimen-supply site 2 to the functional site 1. Upon contact with the reagent, a mucopolysaccharide, such as chondroitin sulfate, is aggregated, the specimen is captured by the functional site provided with a function of filtration, and the specimen cannot develop to the labeled reagent site 3. Thus, nonspecific reaction can be inhibited. In the case of the apparatus shown in FIG. 3, a functional site is composed of a specific member. Incorporation of a specific reagent into the apparatus results in the provision of a pretreatment function of removing impurities from the specimen.

Figure 8:
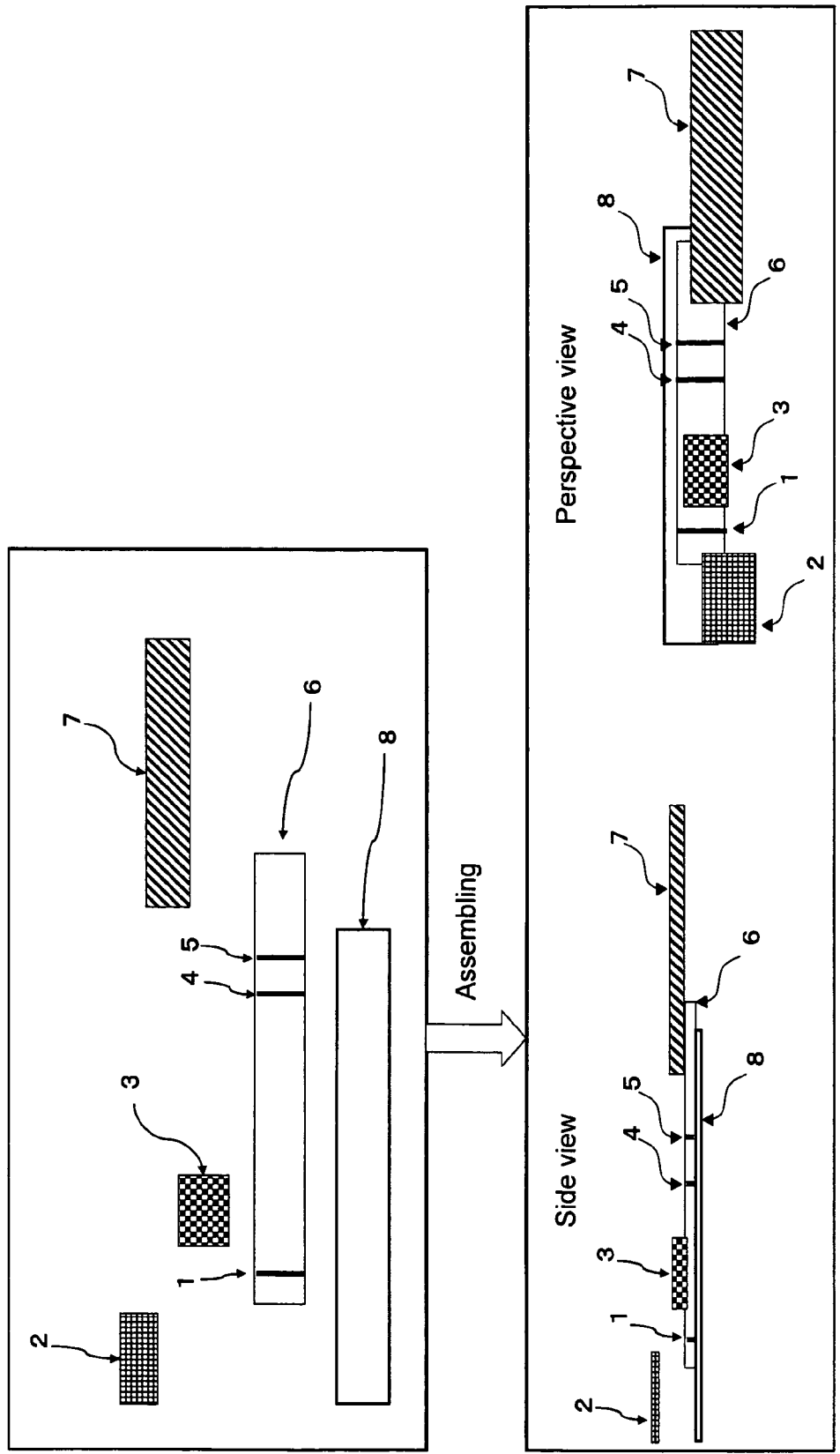
FIG. 8 shows a detection apparatus comprising impurities-absorbing materials on a solid-phase support.

In the case of a specimen containing many solid substances, such as stool, a member having a function of filtration, such as a filter, may be used as a functional site. A person skilled in the art can easily select a member that can function as a filter. In the case of a specimen containing specific impurities, a member that is capable of adsorbing or aggregating such impurities to block the development thereof may be used. In order to render the functional site capable of removing impurities from the specimen, a member of the functional site may be impregnated with a substance capable of adsorbing or aggregating impurities, and the member may then be dried. In FIG. 3, a functional site is composed of a member different from that of the solid-phase support. As shown in FIG. 8, a substance that adsorbs or aggregates impurities can be incorporated in the solid-phase support by adsorption or other means. In the case of the apparatus shown in FIG. 8, such substance is incorporated into the solid-phase support at a site between the specimen-supply site 2 and the labeled reagent site 3. Examples of such detection include the detection of bacterial antigens such as *E. coli* or *Pseudomonas aeruginosa* from a bacterial mixture, in which the existence of *Staphylococcus aureus* is suspected, in particular, the detection of penicillin binding proteins (PBP2') existing in the multiple-drug-resistant *Staphylococcus aureus* (MRSA) cell wall from the aforementioned bacterial mixture. Since protein A contained in the cell wall of *Staphylococcus aureus* specifically binds to the Fc portion of immunoglobulin G, such protein A is deduced to undergo a nonspecific reaction with a labeled reagent or capture reagent.

When the sampled specimen is treated with a pretreatment solution prior to the supply thereof to the specimen-supply site in order to extract or isolate the analyte from the specimen, an impurity-adsorbing substance may be added to the pretreatment solution in order to avoid the nonspecific reaction. In such a case, however, preparation of impurity-adsorbing substances is required concerning the impurities that are not supplied to the specimen-supply site and that do not affect the final evaluation among the substances existing in the solution after the reaction between the sampled specimen and the pretreatment solution. Thus, an excess amount of impurity-adsorbing substances is disadvantageously required. Also, the addition of impurity-adsorbing substances may result in disadvantages, such as sedimentation or turbidity due to, for example, salting out in the pretreatment solution at the time of long-term storage, decomposition of the impurity-adsorbing substances, or deterioration of nonspecific adsorption efficiency due to denaturation. According to the method of the present invention, however, a site containing an impurity-adsorbing substance is provided as the functional site 1 between the specimen-supply site 2 and the labeled reagent site 3. Thus, it is sufficient to prepare impurity-adsorbing substances selectively for impurities in the reaction solution that affect the evaluation. This can reduce the amount of impurity-adsorbing substances. Accordingly, unnecessary sedimentation or turbidity of the pretreatment solution at the time of long-term storage, decomposition of impurity-adsorbing substances, or deterioration of nonspecific adsorption efficiency due to denaturation can be avoided.

Specifically, when the aforementioned bacterial mixture is used, a substance that adsorbs protein A is provided as the functional site 1 between the specimen-supply site 2 and the labeled reagent site 3. Thus, the aforementioned problems can be avoided and the amount of impurity-adsorbing substances to be used can be reduced. An example of the substance that adsorbs protein A is immunoglobulin G. The affinity level between immunoglobulin G and protein A varies depending on the origin and the subclass of immunoglobulin G. Thus, use of immunoglobulin G having strong affinity with protein A is preferable. In the case of human-derived immunoglobulin G, the subclasses IgG1, IgG2, and IgG4 generally exhibit strong affinity with protein A. In the case of mouse-derived immunoglobulin G, the subclasses IgG2a, IgG2b, and IgG3 generally exhibit strong affinity with protein A, and the subclass IgG1 exhibits weak affinity. Rat-derived immunoglobulin G hardly binds to protein A regardless of its subclass. The specimen of a bacterial suspension is added to the specimen-supply site, or the specimen-supply site 2 is selectively soaked in the bacterial suspension, to supply the specimen to the specimen-supply site 2. When pretreatment is required, the pretreated bacterial suspension is added to the specimen-supply site, or the specimen-supply site 2 is selectively soaked in the pretreated bacterial suspension, and the specimen is then supplied to the specimen-supply site 2. The specimen develops from the specimen-supply site 2 to the functional site 1, the specimen is brought into contact with an impurity-adsorbing substance, such as an antibody, to adsorb protein A, and the specimen cannot develop to the labeled reagent site 3 and to the capture reagent site 4. Thus, nonspecific reaction can be inhibited. Protein G contained in the cell wall of the chain coccus of Group G also specifically binds to the Fc portion of immunoglobulin G. Thus, protein G is also deduced to nonspecifically bind to a labeled reagent or captured reagent. The aforementioned method can be similarly employed in order to avoid such nonspecific binding. Since protein A specifically binds to the Fc portion of immunoglobulin G, the Fc portion of an antibody having strong affinity is used as an impurity-adsorbing substance, and an antibody lacking the Fc portion is used as a capture reagent and/or a labeled reagent. This enables the construction of a detection system in which nonspecific binding is inhibited. A specimen may contain an antibody against an antibody to be used as a capture reagent or labeled reagent. In such a case, a substance that specifically adsorbs the capture antibody and the antibody against the antibody used as a labeled reagent is used as a impurity-adsorbing substance and provided as the functional site 1. Thus, nonspecific reaction can be inhibited. For example, an anti-mouse heterophil antibody HAMA (human anti-mouse antibody) is demonstrated to be present in human blood serum at a frequency of several percent to several tens percent. Use of an antibody against HAMA as an impurity-adsorbing substance and provision thereof as a functional site 1 can inhibit nonspecific reaction.

In the case of a blood specimen, fibrins or erythrocytes are contained as impurities. In order to remove such impurities, an anti-fibrin antibody or anti-erythrocyte antibody may be used. In the case of a stool specimen, muscle tissue, bone chip, dead bacteria, fat, or the like is contained. In order to remove such impurities, kaolin or bentonite mineral may be used.

Figure 4:
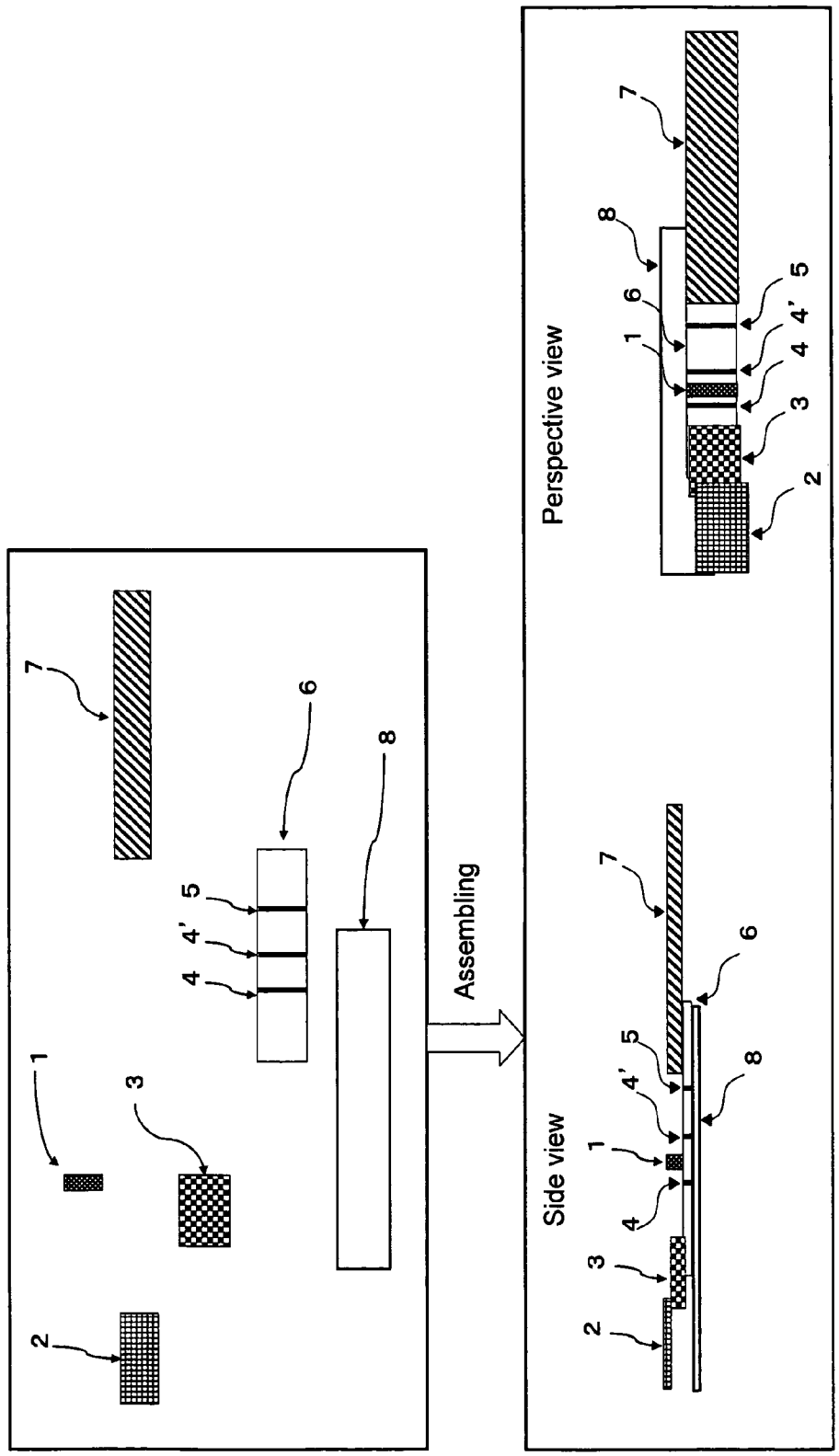
FIG. 4 shows a multidetection apparatus of the present invention capable of detecting a plurality of analytes and capable of optimizing the reaction conditions of the analytes.

FIG. 4 shows a multidetection apparatus that is capable of detecting a plurality of analytes, wherein the reaction conditions of such analytes can be optimized. As an embodiment, detection of influenza virus type A antigen and type B antigen is shown. In such a case, the labeled reagent site 3 containing a type A labeling reagent complex and a type B labeling reagent complex, the capture reagent site 4 capturing a complex of type A antigen and a type A labeling reagent, and the capture reagent site 4' capturing a complex of type B antigen and a type B labeling reagent are provided on the solid-phase support. Also, the functional site 1, i.e., a member impregnated with a reagent such as NaCl and dried, is provided between the capture reagent site 4 and the capture reagent site 4', in order to inhibit the binding between the complex of type A antigen and a type A labeling reagent and the capture reagent site 4'. In this case, a reagent is directly incorporated in the solid-phase support. A suspension specimen to which type A antigen is likely to bind but type B antigen is less likely to bind is supplied to the specimen-supply site 2 in advance, type A antigen and type B antigen develop to form a complex of type A antigen and type A labeling reagent and a complex of type B antigen and type B labeling reagent at the labeled reagent site 3. The complex of type A antigen and type A labeling reagent is captured at the capture reagent site 4. While some complexes of type A antigen and type A labeling reagent and some complexes of type B antigen and type B labeling reagent develop to the capture reagent site 4', they pass through the functional site 1. Thus, a reagent, such as NaCl, that inhibits the binding between the complex of type A antigen and type A labeling reagent and the captured reagent site 4' is discharged in a developer, and the cross reaction between the complex of type A antigen and type A labeling reagent and the captured reagent site 4' is inhibited. In addition to salts such as NaCl, an ionic surfactant can inhibit the cross reaction. Also, the pH level may be adjusted. To this end, a reagent, such as a buffer, acidic substance, basic substance, inorganic salt, organic salt, or amino acid, may be incorporated into the functional site. The concentration of such reagents or the type of salt to be incorporated in the functional sites may be adequately determined in accordance with the type or the optimal conditions of the specimen. In general, the salt concentration may be adjusted to the optimal range of 1.5 M to 50 mM, the pH level may be adjusted to 5.5 to 8.5, and the amino acid concentration may be adjusted to 5% (w/vol) to 10% (w/vol), at the time of reaction.

When a plurality of analytes that would not cause cross reactions are to be detected at a time, the optimal conditions for the antigen-antibody reactions may vary in accordance with the type of a substance. In such a case, a functional site containing a reagent for optimizing the reaction conditions may be provided upstream of the capture reagent site for a relevant analyte.

Figure 5:
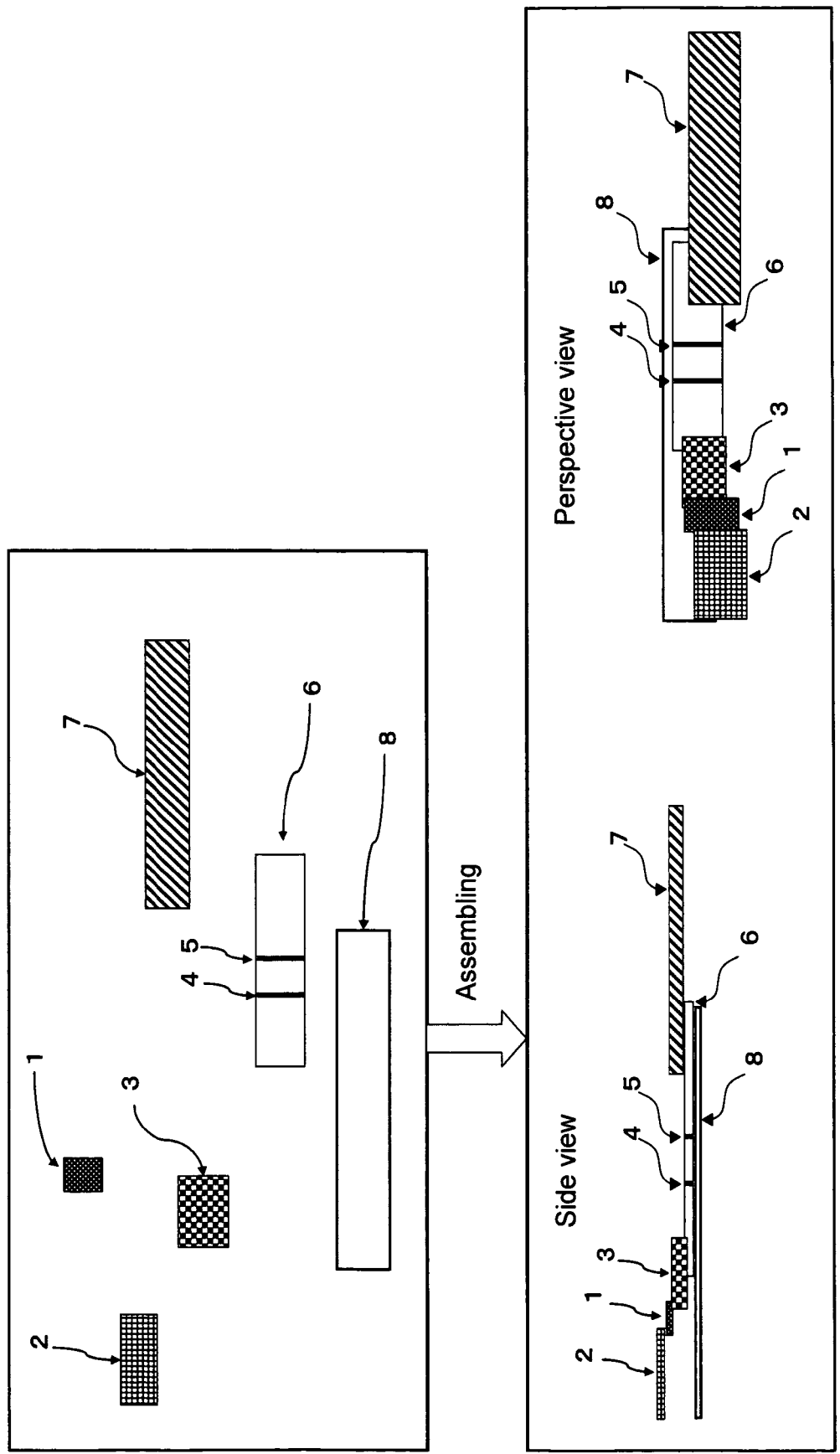
FIG. 5 shows a detection apparatus capable of optimizing the pretreated specimen.

FIG. 5 shows the apparatus of the present invention that can optimize the pretreated specimen. For example, detection of PBP2' existing in the MRSA cell wall is shown. Since extraction of PBP2' is carried out with the use of a basic solution in this case, the specimen becomes to exhibit strong basicity, and the antigen-antibody reaction is inhibited in that state.

Accordingly, a functional site 1, i.e., a member impregnated with an acidic reagent that neutralizes a pH level under alkaline conditions, is provided between the specimen-supply site 2 and the labeled reagent site 3. Instead of the use of such a member, a solid-phase support may be impregnated with an acidic reagent to provide a functional site. In order to disrupt the cell wall, MRSA bacteria are suspended in a strong alkaline solution, and the resultant is supplied to the specimen-supply site 2. The specimen develops from the specimen-supply site 2 to the functional site 1, the specimen is then brought into contact with a reagent, and the pH level of the developing suspension is adjusted to a neutral region. Thus, PBP2' develops to the labeled reagent site 3 under neutral conditions, and it can specifically and stably bind to a labeled reagent.

Further, the apparatus of the present invention may have a function of pretreating a specimen. To this end, the functional site 1 containing a reagent for treating a specimen, such as a basic substance, acidic substance, or surfactant, is provided between the specimen-supply site 2 and the labeled reagent site 3. In such a case, a specimen, the conditions thereof such as the pH level had been changed due to pretreatment, must be optimized for the reaction, and the other functional site for optimizing the aforementioned conditions may be provided downstream of the site for pretreatment on the solid-phase support.

When detection of bacterial antigens, such as *E. coli* or *Salmonella*, in particular, flagella antigens (H antigens) susceptible to heating, is intended, for example, the functional site 1 composed of a porous filter and prepared via impregnation with a reagent such as formalin and drying is provided between the specimen-supply site 2 and the labeled reagent site 3. A specimen, i.e., a throat swab, is suspended in any solution, and the resulting suspension is added to the specimen-supply site, or the specimen-supply site 2 is selectively immersed in the suspension, to supply the specimen to the specimen-supply site 2. The specimen develops from the specimen-supply site 2 to the functional site 1, the specimen is then brought into contact with a reagent, and thus, the bacterial cell surface is stably inactivated without the disruption of H antigen by formalin. Thus, H antigen can be detected.

When carbohydrate antigen of, for example, *E. coli*, hemolytic streptococci, *Legionella*, or *Campylobacter*, is to be detected, for example, the carbohydrate antigen is extracted with the use of an acidic solution. Thus, the specimen becomes acidified, and the antigen-antibody reaction is inhibited in that state. Accordingly, a functional site 1, i.e., a member impregnated with a basic reagent that neutralizes a pH level under acidic conditions is provided between the specimen-supply site 2 and the labeled reagent site 3. Instead of the use of such a member, a solid-phase support may be impregnated with a basic reagent to provide a functional site. In order to separate the carbohydrate antigen from the bacterial cells, bacteria are suspended in a acidic solution, and the resultant is supplied to the specimen-supply site 2. The specimen develops from the specimen-supply site 2 to the functional site 1, the specimen is then brought into contact with a reagent, and the pH level of the developing suspension is adjusted to a neutral region. Thus, the carbohydrate antigen develops to the labeled reagent site 3 under neutral conditions, and it can specifically and stably bind to a labeled reagent.

Figure 6:
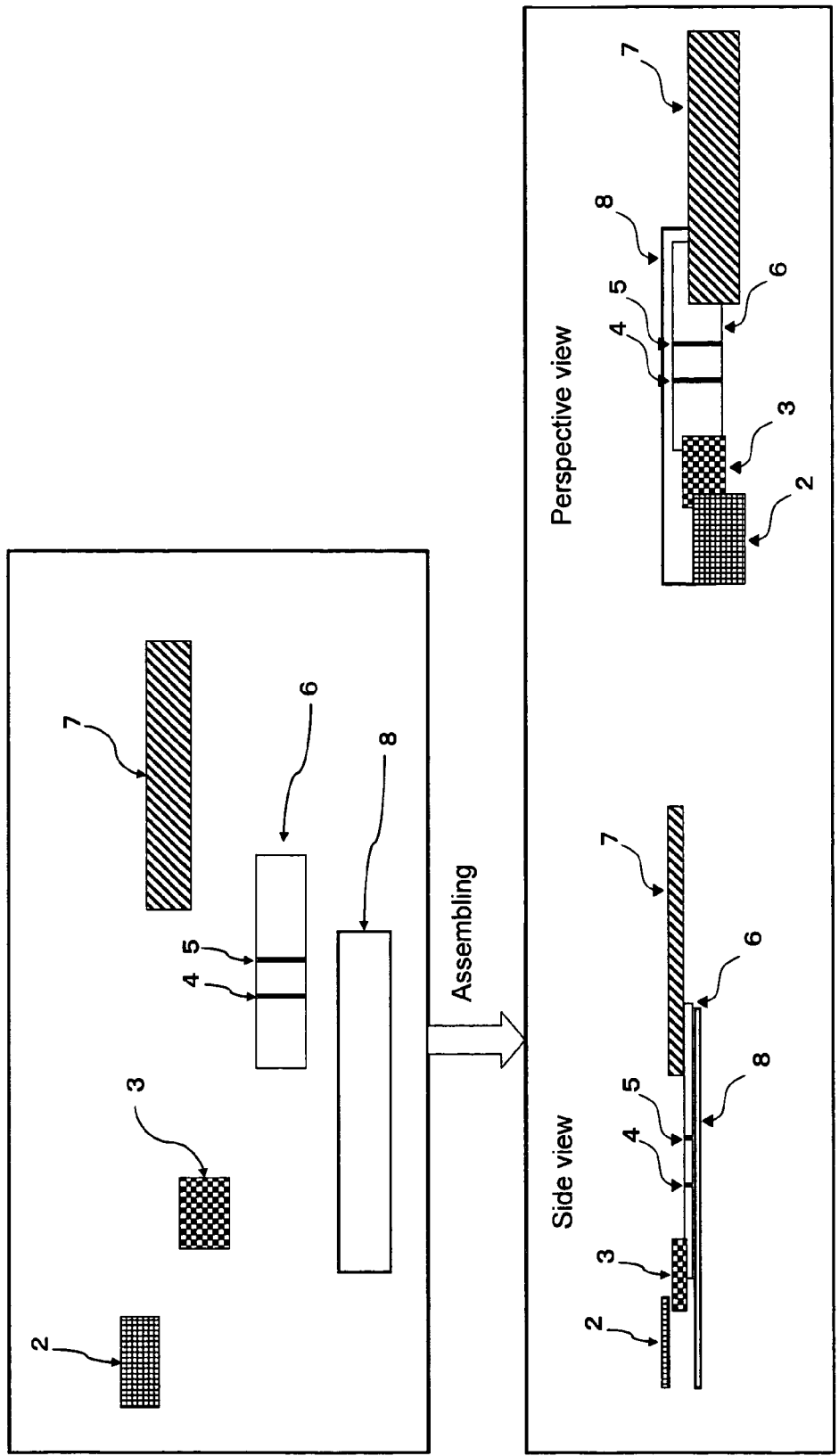
FIG. 6 shows a detection apparatus capable of optimizing the pretreated specimen.

FIG. 6 shows a detection apparatus capable of optimizing the pretreated specimens. In such an apparatus, a functional site 1', i.e., a member impregnated with sodium nitrite, is provided between the specimen-supply site 2 and the functional site 1, since extraction of a carbohydrate antigen with the use of nitrous acid involves risks due to strong acidity. Instead of the use of such a member, a functional site impregnated with sodium nitrite may be provided on the solid-phase support. After the bacteria are suspended in a solution of acetic acid or the like, the resulting suspension is supplied to the specimen-supply site 2. The specimen develops from the specimen-supply site 2 to the functional site 1', and the specimen is then brought into contact with a reagent, which results in the generation of free nitrous acids resulting from the reaction between acetic acid and sodium nitrite in the developing suspension, and carbohydrate antigen can be separated from bacteria with the aid of nitrous acid. Also, the carbohydrate antigen separated by nitrous acid develops from the functional site 1' to the functional site 1, the antigen is then brought into contact with a neutralizing reagent, and the pH level of the developing suspension is adjusted to a neutral region. Thus, the carbohydrate antigen develops to the labeled reagent site 3 under neutral conditions, and it can stably and specifically bind to the labeled reagent.

In the immunochromatography apparatus, an analyte binds to a labeled reagent and a capture reagent. Typically, a ligand that binds to an analyte is an antibody that specifically binds to an antigen when the analyte is an antigen. When the analyte is an antibody, such a ligand is an antigen or antibody that specifically binds to the antibody. When the analyte is a nucleic acid, such a ligand is a nucleic acid, antibody, or conjugate protein that specifically binds to the nucleic acid. In addition, examples of analyte-ligand complex include a receptor-ligand complex and a ligand-receptor complex. The term "labeled reagent" refers to a conjugate of the ligand and an adequate labeling substance. Examples of labeling substances include: metal colloids such as gold colloids; nonmetal colloids such as selenium colloids; insoluble particulate substances such as colored resin particles, dye colloids, or colored liposomes; enzymes that catalyze color reactions such as alkaline phosphatase or peroxidase; fluorescent dyes; and radioisotopes. A capture reagent and a labeled reagent may be the same substance. When the analyte has only one site that binds to the aforementioned substance, a complex of a labeled reagent, an analyte, and a capture reagent is not formed. In such a case, a capture reagent and a labeled reagent are required to bind to separate sites of the analyte. A solid-phase support may be composed of any substance as long as the specimen sample can be absorbed and can flow due to the capillary phenomenon. For example, a material constituting the solid-phase support is selected from the group consisting of natural or synthetic polymers, such as nitrocellulose, cellulose acetate, nylon, polyethersulfone, polyvinyl alcohol, polyester, glass fiber, polyolefin, cellulose, or polystyrene, and mixtures of any of such substances. The solid-phase support preferably has a shape of strip. The capture reagent may be immobilized on the solid-phase support by conventional techniques, such as adsorption or chemical binding with the utilization of a functional group, such as an amino or carboxyl group.

The detection apparatus used in the method according to the present invention may further comprise a control reagent. Furthermore, the apparatus may comprise a specimen absorption site. A control reagent is not particularly limited. For example, a substance to which a ligand in the labeled reagent binds can be used. A control reagent may be immobilized downstream of the capture reagent site. The absorption site is capable of absorbing liquid, i.e., it absorbs a specimen that has passed through a capture section to regulate the flow of the specimen. The absorption site may be provided at the lowermost stream of the detection apparatus. For example, an absorption section made of paper may be employed as an absorbent pad.

Further, the apparatus of the present invention may be resin-laminated on its front or part thereof, in order to protect the reagent from external environmental conditions, such as drying. The apparatus may be accommodated in a container (housing).

EXAMPLES

The present invention is described in greater detail with reference to the following examples, although the technical scope of the present invention is not limited to these examples.

Example 1

Elimination of Nonspecific Reaction of Chondroitin Sulfate in Detection of Influenza A Virus (FIG. 3)

(1) Preparation of Colloidal Gold Antibodies

Colloidal gold (10 ml) was fractionated, and the pH level was adjusted to 7.0 with the aid of 100 mM potassium carbonate. Anti-influenza A virus monoclonal antibodies were dialyzed with a 2 mM boric acid solution, centrifuged, and purified. A 2 mM boric acid solution was added thereto to prepare a solution containing the antibodies at a concentration of 100 μg/ml. A fraction of the resulting solution containing the anti-influenza A virus monoclonal antibodies at a final concentration of 10 μg/ml was thoroughly agitated and added to the colloidal gold. Five minutes thereafter, 1 ml of 10% BSA was added and the mixture was moderately agitated with a rotator for 10 minutes. The entire amount of the solution was transferred to a centrifugation tube and centrifugation was carried out at 14,000 rpm for 30 minutes at 4° C. After the centrifugation, the supernatant was suctioned, and 1 ml of a 10 mM borate buffer was added to the colloidal gold that had been precipitated and the colloidal gold that had been sensitized with the anti-influenza A virus monoclonal antibodies to prepare a suspension.

(2) Dehydration of Colloidal Gold Antibodies

The antibody-sensitized colloidal gold prepared in the section above ($OD_{520}$=6.0) was sprayed on a polystyrene unwoven fabric of 10 mm×300 mm at a flow rate of 10 μl/cm using a positive pressure spray apparatus (Biojet, BioDot Inc.). Subsequently, the antibody-sensitized colloidal gold was dehydrated under reduced pressure in a decompressor for 1 hour to prepare a dehydrated antibody-sensitized colloidal gold pad. The pad was cut at intervals of 4 mm and used as the labeled reagent site 3.

(3) Preparation of DEAE-Dextran Pad

A glass fiber filter was immersed in a 2% to 10% DEAE-Dextran solution, dried at 45° C. overnight, and then cut into pieces of 10 mm×4 mm each. The resultant was used as a functional site 1.

(4) Determination of Solid-Phase Support 6, Capture Reagent Site 4, and Control Site 5

A capture reagent, i.e., a 10 mM Tris buffer (pH 7.5) containing anti-influenza virus monoclonal antibodies at $OD_{280}$ of 2.0, and a control reagent, i.e., a 10 mM phosphate buffer (pH 7.5) containing anti-mouse IgG (Dako) at 3.8 mg/ml, were applied to the High Flow HF 12004 (20 mm×200 mm, Millipore) at 1.04 μl/cm using a positive pressure spray apparatus (Biojet, BioDot Inc.). The resultant was dried at 45° C. for 60 minutes, cut into pieces of 20 mm×4 mm each, and then used as a solid-phase support 6.

(5) Preparation of Immunochromatography Detection Apparatus

Figure 7:
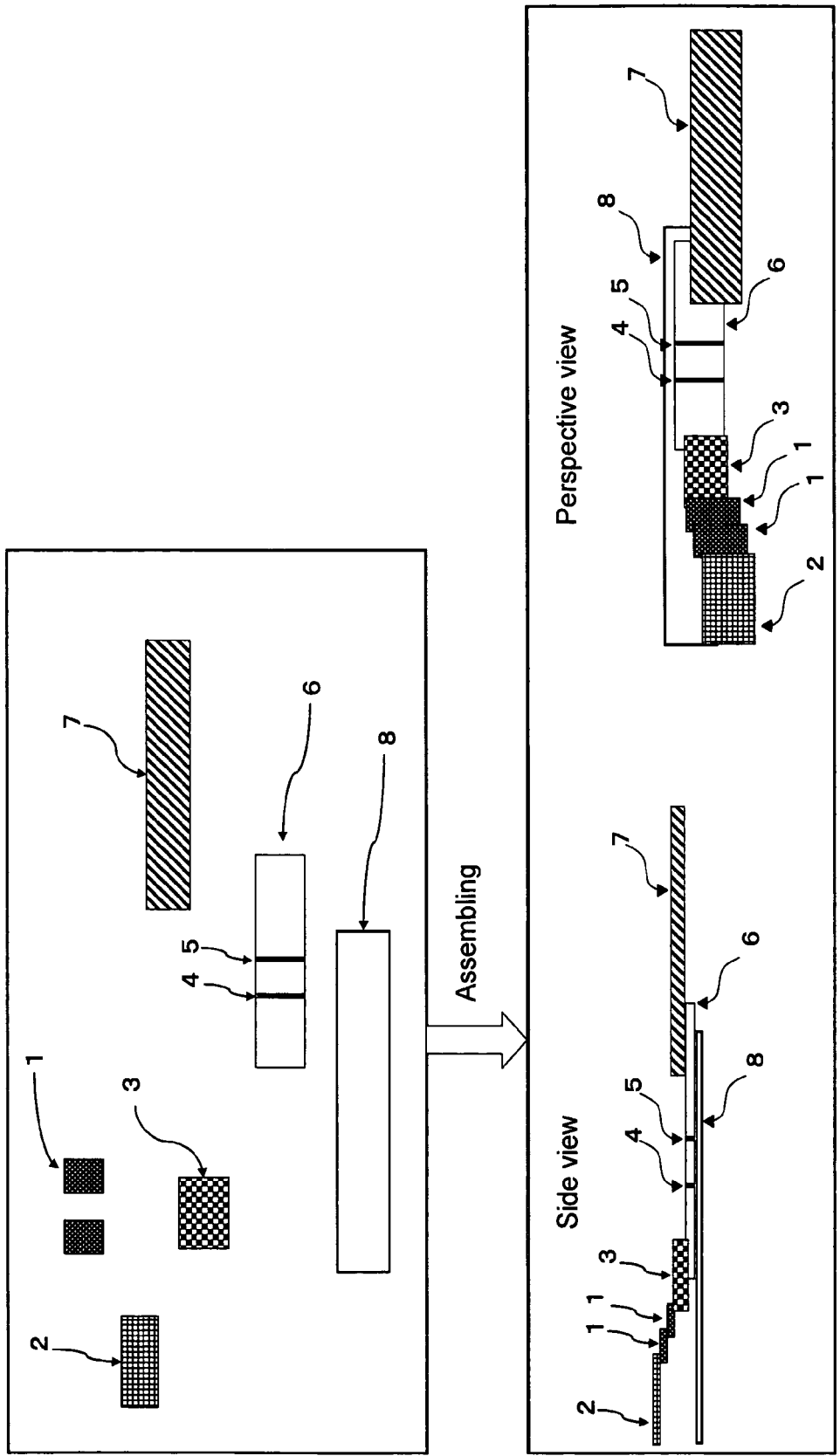
FIG. 7 shows a conventional immunochromatography detection apparatus.

On a top laminate 8, a solid-phase support 6 comprising a capture reagent site 4 and a control site 5 was provided, a labeled reagent site 3, a functional site 1, a glass fiber filter as a specimen-supply site 2, and a relatively thick filter as an absorption site 7 were provided at arbitrary positions. As a conventional apparatus, an immunochromatography detection apparatus lacking a functional site 1 was prepared and used as a control (FIG. 7).

(6) Detection Method

As a positive specimen, a suspension of influenza A virus antigens in a phosphate buffer was used. As a nonspecific specimen, a suspension of 2% chondroitin sulfate in a phosphate buffer was used. The specimen-supply site 2 of the apparatus of the present invention comprising a functional site 1 prepared in the section above and that of a conventional apparatus lacking a functional site 1 were immersed in 150 μl of each specimen. Nonspecific reactions caused by chondroitin sulfate were compared and tested.

(7) Test Results

The conventional apparatus showed the positive results on the positive specimen and on the nonspecific specimen. In contrast, the apparatus of the present invention showed the positive results on the positive specimen and the negative results on the nonspecific specimen.

Example 2

Detection of PBP2' of MRSA (FIG. 5)

(1) Preparation of Colloidal Gold Antibodies

Colloidal gold (10 ml) was fractionated, and the pH level was adjusted to 8.0 with the addition of 100mM potassium carbonate. The anti-PBP2' antibodies were dialyzed with a 2 mM boric acid solution, centrifuged, and purified. A 2 mM boric acid solution was added thereto to prepare a solution containing the antibodies at a concentration of 40μg/ml. A fraction of the resulting solution containing the anti-PBP2' antibodies at a final concentration of 2μg/ml was thoroughly agitated and added to the colloidal gold. Five minutes thereafter, 1 ml of 10% BSA was added and the mixture was moderately agitated with a rotator for 10minutes. The entire amount of the solution was transferred to a centrifugation tube and centrifugation was carried out at 14,000 rpm for 30 minutes at 4° C. After the centrifugation, the supernatant was suctioned, and 1 ml of a 10 mM borate buffer was added to the colloidal gold that had been precipitated and the colloidal gold that had been sensitized with the anti-PBP2' antibodies to prepare a suspension.

The antibody-sensitized colloidal gold prepared in the section above ($OD_{520}$=0.5) was sprayed on a polystyrene unwoven fabric of 10 mm×300 mm at a flow rate of 10 μl/cm using a positive pressure spray apparatus (Biojet, BioDot Inc.). Subsequently, the antibody-sensitized colloidal gold was dehydrated under reduced pressure in a decompressor for 1 hour to prepare a dehydrated antibody-sensitized colloidal gold pad. The pad was cut at intervals of 4 mm and used as the labeled reagent site 3.

(3) Preparation of Neutralizing Pad

A filter was immersed in a phosphate buffer containing a 0.5% nonionic surfactant, dried at 45° C. overnight, and cut into pieces of 1.8 mm×4 mm each. The resultant was used as a functional site 1.

19

(4) Determination of Solid-Phase Support 6, Capture Reagent Site 4, and Control Site 5

A capture reagent, i.e., a 10 mM phosphate buffer (pH 7.5) containing anti-PBP2' antibodies at 7.2 µg/m, and a control reagent, i.e., a 10 mM phosphate buffer (pH 7.5) containing anti-mouse IgG (Dako) at 3.8 mg/ml, were applied to the High Flow HF 12004 (20 mm×200 mm, Millipore) at 1.04 µl/cm using a positive pressure spray apparatus (Biojet, BioDot Inc.). The resultant was dried at 45° C. for 60 minutes, cut into pieces of 20 mm×4 mm each, and then used as a solid-phase support 6.

(5) Preparation of Immunochromatography Detection Apparatus

On a top laminate 8, a solid-phase support 6 comprising a capture reagent site 4 and a control site 5 was provided, a labeled reagent site 3, a functional site 1, a glass fiber filter as a specimen-supply site 2, and a relatively thick filter as an absorption site 7 were provided at arbitrary positions. As a conventional apparatus, an immunochromatography detection apparatus lacking a functional site 1 was prepared and used as a control (FIG. 7).

(6) Detection Method

As a positive specimen, two platinum loopfuls of MRSA were sampled, and two platinum loopfuls of MSSA were sampled as a negative specimen. These samples were suspended in 150 µl of 0.1N NaOH and heated at 95° C. for 3 minutes. After cooling, the specimen-supply site 2 of the apparatus of the present invention comprising a functional site 1 prepared in the section above and that of the conventional apparatus lacking a functional site 1 were immersed in specimens, and functions of the neutralizing pads were compared and tested.

(7) Test Results

The conventional apparatus showed the negative results on the negative specimen and on the positive specimen. In contrast, the apparatus of the present invention showed the negative results on the negative specimen and the positive results on the positive specimen.

Example 3

Avoidance of Nonspecific Reaction Caused by Protein A in the Detection of PBP2' of MRSA (FIG. 8)

(1) Preparation of Colloidal Gold Antibodies

Colloidal gold (10 ml) was fractionated, and the pH level was adjusted to 8.0 with the addition of 100mM potassium carbonate. The anti-PBP2' antibodies were dialyzed with a 2 mM boric acid solution, centrifuged, and purified. A 2 mM boric acid solution was added thereto to prepare a solution containing the antibodies at a concentration of 40µg/ml. A fraction of the resulting solution containing the anti-PBP2' antibodies at a final concentration of 2µg/ml was thoroughly agitated and added to the colloidal gold. Five minutes thereafter, 1 ml of 10% BSA was added and the mixture was moderately agitated with a rotator for 10minutes. The entire amount of the solution was transferred to a centrifugation tube and centrifugation was carried out at 14,000 rpm for 30 minutes at 4° C. After the centrifugation, the supernatant was suctioned, and 1 ml of a 10 mM borate buffer was added to the colloidal gold that had been precipitated and the colloidal gold that had been sensitized with the anti-PBP2' antibodies to prepare a suspension.

The antibody-sensitized colloidal gold prepared in the section above ($OD_{520}$=0.5) was sprayed on a polystyrene unwoven fabric of 10 mm×300 mm at a flow rate of 10 µl/cm using a positive pressure spray apparatus (Biojet, BioDot Inc.). Subsequently, the antibody-sensitized colloidal gold was dehydrated under reduced pressure in a decompressor for 1 hour to prepare a dehydrated antibody-sensitized colloidal gold pad. The pad was cut at intervals of 4 mm and used as the labeled reagent site 3.

(3) Determination of Solid-Phase Support 6, Functional Site 1, Capture Reagent Site 4, and Control Site 5

A functional site 1, i.e., a 10 mM phosphate buffer (pH 7.5) containing mouse IgG2a at 3.8 mg/ml, which does not recognize PBP2' and exhibits high affinity with protein A, a capture reagent, i.e., a 10 mM phosphate buffer (pH 7.5) containing anti-PBP2' antibodies at 7.2 µg/ml, and a control reagent, i.e., a 10 mM phosphate buffer (pH 7.5) containing anti-mouse IgG (Dako) at 3.8 mg/ml, were applied to the High Flow HF 12004 (20 mm×200 mm, Millipore) at 1.04 µl/cm using a positive pressure spray apparatus (Biojet, BioDot Inc.). The resultant was dried at 45° C. for 60 minutes, cut into pieces of 20 mm×4 mm each, and then used as a solid-phase support 6.

(4) Preparation of Immunochromatography Detection Apparatus

On a top laminate 8, a functional site 1, a solid-phase support 6 comprising a capture reagent site 4 and a control site 5, a labeled reagent site 3, a functional site 1, a glass fiber filter as a specimen-supply site 2, and a relatively thick filter as an absorption site 7 were provided at arbitrary positions. As a conventional apparatus, an immunochromatography detection apparatus lacking a functional site 1 was prepared and used as a control (FIG. 8).

(5) Detection Method

As a positive specimen, two platinum loopfuls of MRSA were sampled, and two platinum loopfuls of MSSA were sampled as a negative specimen. These samples were suspended in a 150 µl of dilute alkaline solution and heated at 95° C. for 3 minutes. After cooling, the specimen suspensions were neutralized with a phosphate buffer, and the specimen-supply site 2 of the apparatus of the present invention comprising a functional site 1 prepared in the section above and that of the conventional apparatus lacking a functional site 1 were immersed in specimens, and nonspecific reactions caused by protein A were compared and tested.

(6) Test Results

The conventional apparatus showed the positive results on the positive specimen and on the negative specimen. In contrast, the apparatus of the present invention showed the positive results on the positive specimen and the negative results on the negative specimen.

All publications, patents, and patent applications cited herein are incorporated herein by reference in their entirety.

The invention claimed is:

1. A chromatography detection apparatus comprising a sheet-like solid-phase support that comprises: (i) a specimen-supply site on the support, at which is supplied a specimen deduced to contain at least an analyte (ii) a capture reagent site comprising a capture reagent immobilized on the capture reagent site and capable of specifically binding to and capturing a complex of the analyte and a labeled reagent; and (iii) a functional site provided between the specimen-supply site and the capture reagent site, wherein the functional site comprises a reagent for aggregating polysaccharides in a nasal or throat swab and a filter for removing said aggregated polysaccharides, wherein (i) said reagent for aggregating polysaccharides is DEAE-Dextran and (ii) the DEAE-Dextran is impregnated in the filter.

2. The chromatography detection apparatus according to claim 1, further comprising: a labeled reagent site at which a labeled reagent containing a ligand that specifically binds to the analyte is sustained so as to be capable of developing on the solid-phase support.

3. The chromatography detection apparatus according to claim 2, wherein the specimen-supply site is provided at a site spatially separate from the labeled reagent site.

4. The chromatography detection apparatus according to claim 1, which is suitable to use a specimen containing bacteria or virus.

5. The chromatography detection apparatus according to claim 1, wherein the labeled reagent is a ligand labeled with an enzyme or insoluble particulate substance.

6. The chromatography detection apparatus according to claim 1, wherein the binding between the analyte and the labeled reagent and the binding between the complex of the analyte and the labeled reagent and the capture reagent result from an antigen-antibody reaction.

7. The chromatography detection apparatus according to claim 1, wherein the solid-phase support comprises a material selected from the group consisting of nitrocellulose, cellulose acetate, nylon, and polyethersulfone.

* * * * *